(12) United States Patent
Neumann

(10) Patent No.: US 12,322,491 B2
(45) Date of Patent: Jun. 3, 2025

(54) SYSTEM AND METHOD FOR GENERATING A GEOGRAPHICALLY LINKED NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 744 days.

(21) Appl. No.: 17/187,989

(22) Filed: Mar. 1, 2021

(65) Prior Publication Data

US 2022/0277830 A1    Sep. 1, 2022

(51) Int. Cl.
| G06Q 10/00 | (2023.01) |
| G16H 20/60 | (2018.01) |
| G16H 50/80 | (2018.01) |
| G06N 20/00 | (2019.01) |

(52) U.S. Cl.
CPC ............ *G16H 20/60* (2018.01); *G16H 50/80* (2018.01); *C12Q 2600/156* (2013.01); *G06N 20/00* (2019.01)

(58) Field of Classification Search
CPC ......... G16H 20/60; G16H 50/80; G16H 10/40
See application file for complete search history.

(56) References Cited

U.S. PATENT DOCUMENTS

| 7,054,758 | B2 | 5/2006 | Gill-Garrison |
| 7,074,183 | B2 | 7/2006 | Castellanos |
| 7,970,620 | B2 | 6/2011 | Brown |
| 8,000,982 | B2 | 8/2011 | Kane |
| 8,226,414 | B2 | 7/2012 | Bodin |
| 8,560,336 | B2 | 10/2013 | Schwarzberg |
| 8,684,922 | B2 | 4/2014 | Tran |

(Continued)

FOREIGN PATENT DOCUMENTS

| CN | 109545328 | 3/2019 |
| IN | 202041024942 | 6/2020 |

(Continued)

OTHER PUBLICATIONS

Title:Blastocystis: how do specific diets and human gut microbiota affect its development and pathogenicity? Date: Jan. 23, 2017 By: Lepczynska.

(Continued)

*Primary Examiner* — Rajesh Khattar
(74) *Attorney, Agent, or Firm* — Caldwell Intellectual Property Law

(57) ABSTRACT

A system for generating a geographically linked nourishment program comprising a computing device configured to obtain a biochemical element, identify a vigor panel as a function of the biochemical element, wherein identifying further comprises receiving a geographical indicator, ascertaining a geographical predictive element as a function of the geographical indicator, and identifying the vigor panel as a function of the geographical predictive element and the biochemical element using a geographical machine-learning model, determine an edible as a function of the vigor panel, and generate a nourishment program as a function of the edible.

14 Claims, 7 Drawing Sheets

(56) References Cited

U.S. PATENT DOCUMENTS

| | | |
|---|---|---|
| 10,357,157 B2 | 7/2019 | Apte |
| 10,373,522 B2 | 8/2019 | Byron |
| 2002/0046060 A1 | 4/2002 | Hoskyns |
| 2006/0074279 A1 | 4/2006 | Brover |
| 2006/0199155 A1 | 9/2006 | Mosher |
| 2008/0275912 A1 | 11/2008 | Roberts |
| 2010/0070455 A1 | 3/2010 | Halperin |
| 2010/0136508 A1 | 6/2010 | Zekhtser |
| 2012/0276059 A1 | 11/2012 | Boone |
| 2014/0220163 A1 | 8/2014 | Soleimani Babadi |
| 2015/0161355 A1 | 6/2015 | Karra |
| 2015/0356885 A1 | 12/2015 | Chen |
| 2016/0091419 A1 | 3/2016 | Watson |
| 2016/0225284 A1 | 8/2016 | Schoen |
| 2016/0306931 A1 | 10/2016 | Lahteenmaki |
| 2017/0159108 A1 | 6/2017 | Budding |
| 2017/0249445 A1 | 8/2017 | Devries |
| 2018/0308389 A1 | 10/2018 | Moser |
| 2018/0310890 A1* | 11/2018 | Li .................. A61B 5/4842 |
| 2019/0074080 A1 | 3/2019 | Appelbaum |
| 2019/0180358 A1* | 6/2019 | Nandan .............. G06F 18/2113 |
| 2019/0221303 A1 | 7/2019 | Bennett |
| 2019/0223843 A1* | 7/2019 | Vitti .................. A61B 5/4839 |
| 2019/0251861 A1 | 8/2019 | Wolf |
| 2019/0252058 A1 | 8/2019 | Wolf |
| 2019/0267140 A1 | 8/2019 | Segal |
| 2019/0290172 A1 | 9/2019 | Hadad |
| 2019/0341145 A1 | 11/2019 | Prakash |
| 2020/0013488 A1 | 1/2020 | Lui |
| 2020/0066181 A1 | 2/2020 | Hadjigeorgiou |
| 2020/0138362 A1 | 5/2020 | Koumpan |
| 2020/0185100 A1 | 6/2020 | Francois |
| 2020/0277658 A1 | 9/2020 | Cutcliffe |
| 2020/0286623 A1 | 9/2020 | Apte |
| 2020/0308627 A1 | 10/2020 | Jain |
| 2020/0312455 A1 | 10/2020 | Bhalotia |
| 2020/0342545 A1 | 10/2020 | Dobson |

FOREIGN PATENT DOCUMENTS

| | | |
|---|---|---|
| IN | 202041031475 | 7/2020 |
| RU | 2691145 C2 | 6/2019 |
| WO | 2014015378 | 1/2014 |
| WO | 2019054737 | 3/2019 |
| WO | 2019110412 | 6/2019 |
| WO | 2019229753 | 12/2019 |
| WO | 2020069500 | 4/2020 |
| WO | 2020201457 | 10/2020 |
| WO | 2020239745 | 12/2020 |

OTHER PUBLICATIONS

Title: Dietary Quercetin Increases Colonic Microbial Diversity and Attenuates Colitis Severity in Citrobacter rodentium-Infected Mice; By: Lin; Date.

https://gut.bmj.com/content/69/8/1520?int_source=trendmd&int_medium=cpc&int_campaign=usage-042019; Title: Big data in IBD: big progress for clinical practice; Date: Jul. 7, 2020; By: Tabib, Nasim Sadat Seyed.

https://www.nature.com/articles/srep35216; Title: The fecal microbiota as a biomarker for disease activity in Crohn's disease; Date: Oct. 13, 2016; By: Tedjo, Danyta I.

https://www.mdpi.com/2072-6643/7/2/1282; Title: Pilot dietary intervention with heat-stabilized rice bran modulates stool microbiota and metabolites in healthy adults; Date: Feb. 16, 2015; By: Sheflin, Amy M.

https://www.ncbi.nlm.nih.gov/pmc/articles/PMC4299332/; Title: Application of metagenomics in the human gut microbiome; Date: Jan. 21, 2015; By: Wang, Wei-Lin.

https://theana.org/COVID-19; Title: Personalized Nutrition & the COVID-19 Era; By: Victoria Yunez Behm; Date: Oct. 1, 2020.

https://www.frontiersin.org/articles/10.3389/fnut.2016.00005/full; Title: Modeling-Enabled Systems Nutritional Immunology; By: Meghna Verma; Date: Feb. 16, 2016.

Title: General Nutrition Management in Patients infected with Human Immunodeficiency Virus; By: Nerad; Date: 2003.

* cited by examiner

SYSTEM AND METHOD FOR GENERATING A GEOGRAPHICALLY LINKED NOURISHMENT PROGRAM

FIELD OF THE INVENTION

The present invention generally relates to the field of artificial intelligence. In particular, the present invention is directed to a system and method for generating a geographically linked nourishment program.

BACKGROUND

Current edible suggestion systems do not account for the status of health systems of individuals as a function of geographics. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a geographically linked nourishment program includes a computing device configured to obtain a biochemical element, identify a vigor panel as a function of the biochemical element, wherein identifying further comprises receiving a geographical indicator, ascertaining a geographical predictive element as a function of the geographical indicator, and identifying the vigor panel as a function of the geographical predictive element and the biochemical element using a geographical machine-learning model, determine an edible as a function of the vigor panel, and generate a nourishment program as a function of the edible.

In another aspect a method for generating a geographically linked nourishment program includes obtaining, by a computing device, a biochemical element, identifying, by the computing device, a vigor panel as a function of the biochemical element, wherein identifying further comprises receiving a geographical indicator, ascertaining a geographical predictive element as a function of the geographical indicator, and identifying the vigor panel as a function of the geographical predictive element and the biochemical element using a geographical machine-learning model, determining, by the computing device, an edible as a function of the vigor panel, and generating, by the computing device, a nourishment program as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a geographically linked nourishment program. In an embodiment, this disclosure obtains a biochemical element from a user. Aspects of the present disclosure can be used to identify a vigor panel. This is so, at least in part because this disclosure utilizes a geographical indicator, geographical predictive element, and a geographical machine-learning model. Aspects of the present disclosure can also be used to determine an edible as a function of the vigor panel. Aspects of the present disclosure allow for generating a nourishment program as a function of the edible. Exemplary embodiments illustrating aspects of the present disclosure are described below in the context of several specific examples.

Figure 1:
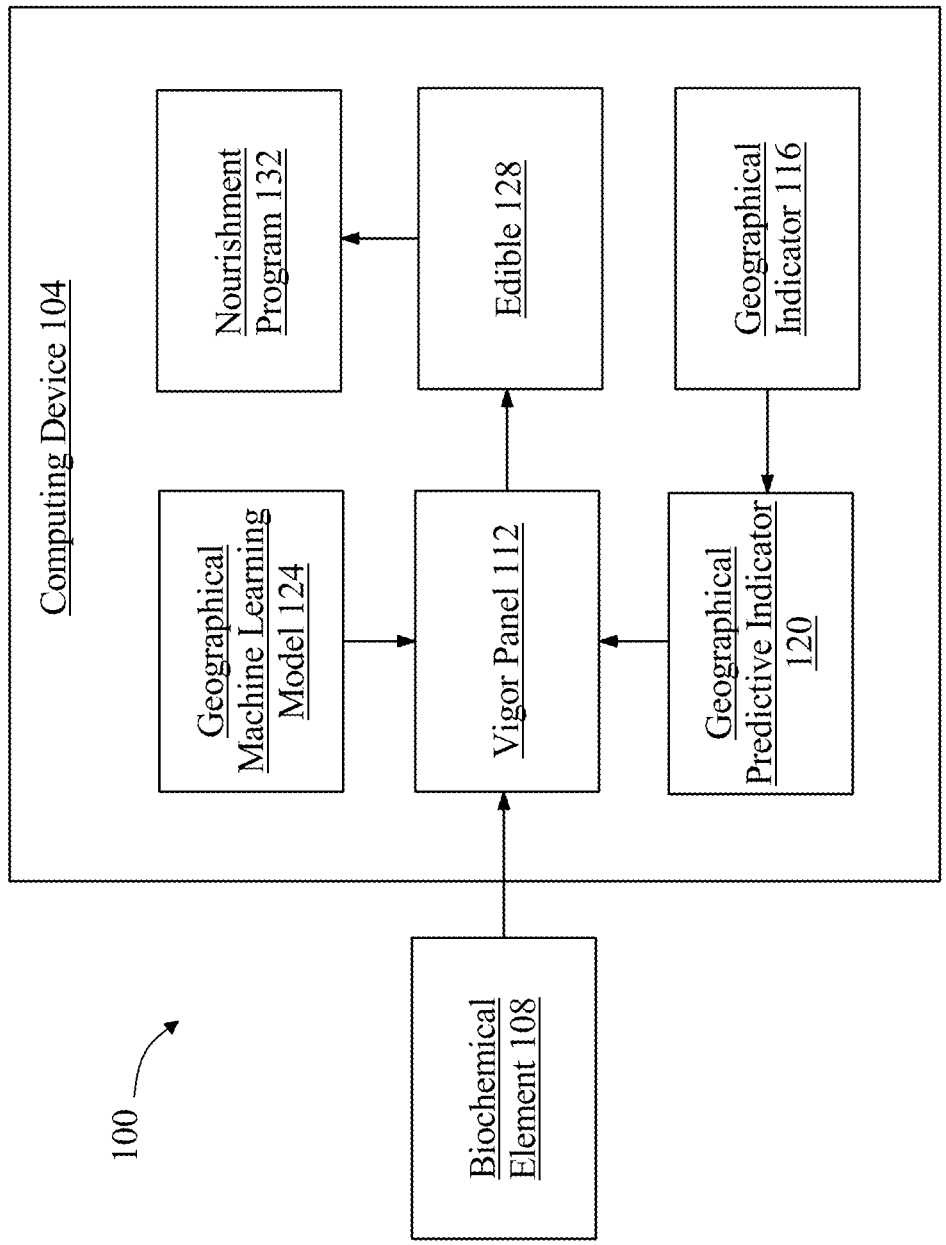
FIG. 1 is a block diagram illustrating an exemplary embodiment of a system for generating a geographical nourishment program.

Referring now to FIG. 1, an exemplary embodiment of a system 100 for generating a geographically linked nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a biochemical element 108. As used in this disclosure an "biochemical element" is an element of data that denotes the health status of an individual's health system. Biochemical element 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Biochemical element 108 may include a biological sampling device. Biochemical element 108 may include one or more biomarkers. As used in this disclosure a "biomarker" is a molecule and/or chemical that identifies the health status of an individual's health system. As a non-limiting example, biomarkers may include, procalcitonin, C-reactive protein, mixed lineage kinase domain-like protein, CXCL5, CCL17, CXCL9, IP-10, CXCL11, IL-8, IL-10, brain natriuretic peptide, blood urea nitrogen, androsterone/5α-dihydrotestosterone sulfate, long noncoding RNA nuclear-enriched abundant transcript 1, intracellular pathogen resistance 1, Tumor necrosis factor-α, Human speckled 110, and the like thereof. As a further non-limiting example, biochemical element 108 may include datum from one or more devices that collect, store, and/or calculate one or more lights, voltages, currents, sounds, chemicals, pressures, and the like thereof that are associated with the user's health system. As used in this disclosure a "health system" is an organ and/or tissue system that relates to the health status of an individual's body. As a non-limiting example, health system may include one or more organs and/or tissue systems including, but not limited to a/an circulatory system, cardiovascular system digestive system, excretory system, endocrine system, geographical system, exocrine system, immune system, lymphatic system, muscular system, nervous system, renal system, urinary system, reproductive system, respiratory system, skeletal system, and the like thereof.

Still referring to FIG. 1, computing device 104 may obtain biochemical element 108 by receiving an input from a user. As used in this disclosure "input" is an element of datum that is obtained by the user. In an embodiment, and without limitation, input may include one or more inputs from a family member. For example, and without limitation, a brother, sister, mother, father, cousin, aunt, uncle, grandparent, child, friend, and the like thereof may enter to computing device 104 that an individual may have an altered and/or changing health system. Input may include one or more inputs from an informed advisor as a function of identifying a medical assessment, wherein a "medical assessment" is an evaluation and/or estimation of the health status of the individual. For example, a medical assessment may include one or more assessments of blood pressure, vision, behavior, biomarkers, viability, vigor, and the like thereof. As used in this disclosure "informed advisor" is an individual that is skilled in the study of the health status of the individual. As a non-limiting example an informed advisor may include a medical professional who may assist and/or participate in the medical treatment of an individual's health system including, but not limited to, family physicians, tropical medicine physicians, infectious disease physicians, medical parasitologists, traveler's health physicians, and the like thereof. As a non-limiting example input may include an informed advisor that enters a medical assessment comprising a brain analysis, cognitive analysis, blood analysis, urine analysis, stool analysis, saliva analysis, skin analysis, and the like thereof. Additionally or alternatively, input may include one or more medical records and/or patient charts that identify an individual's previous health status.

Still referring to FIG. 1, computing device 104 identifies a vigor panel 112 as a function of biochemical element 108. As used in this disclosure a "vigor panel" is a profile and/or estimation of an individual's health status. For example, and without limitation, vigor panel may indicate that an individual's health status is weakened and/or compromised. Computing device 104 may identify vigor panel 112 as a function of determining an origination element. As used in this disclosure an "origination element" is a source of origination of the pathogen and/or infection. As a non-limiting example an origination element may include a country, a person, a travel activity, an insect, an animal, an aerosol, a city, a town, a chemical, and the like thereof. Vigor panel 112 is produced as a function of receiving a geographical indicator. As used in this disclosure a "geographical indicator" is an indicator associated with one or more pathogens in relation to a region and/or location of the earth.

For example, and without limitation, geographical indicator 116 may include an indicator associated with a geographical location, wherein a geographical location is a location and/or place used to denote a region on the earth's surface or elsewhere, as described in detail below, in reference to FIG. 2. In an embodiment and without limitation, geographical indicator 116 includes a contact tracing element. As used in this disclosure a "contact tracing element" is an element associated with the identification of persons who may have come into contact with an infected individual and/or pathogen. As used in this disclosure a "pathogen" is a bacterium, virus, or other microorganism that can cause a dysfunction. As a non-limiting example, contact tracing element may include identifying an individual as having a communicable dysfunction, wherein identification may include without limitation reports to public health officials and/or primary care health provider notifications. As a further non-limiting example, contact tracing element may include interviewing the individual to determine their movements, who they have been in close contact with, and/or who their sexual partners have been. As a further non-limiting example, contact tracing element may include identifying family members, co-workers, public health workers, and/or any other individual that has been in close contact with the infected individual and/or pathogen. As a further non-limiting example, contact tracing element may include one or more travel records. As used in this disclosure a "travel record" is a record and/or history of any travel by the infected individual. As a non-limiting example travel record may include air travel to another country and/or region. As a further non-limiting example, travel record may include auto travel to another city and/or state. As a further non-limiting example, travel record may include naval travel aboard one or more cruise ships and/or naval vessels.

Still referring to FIG. 1, computing device 104 identifies vigor panel 112 by ascertaining a geographical predictive element 120 as a function of geographical indicator 116. As used in this disclosure a "geographical predictive element" is an element associated with the likelihood for an individual to contract and/or be susceptible to a pathogen. For example, and without limitation, geographical predictive element 120 may include a high likelihood for contracting a pathogen associated with malaria. As a further non-limiting example, geographical predictive element 120 may include a low likelihood for contracting a pathogen associated with African sleeping sickness. In an embodiment and without limitation, geographical predictive element 120 may include a basic exponential model and/or an SIR model to predict the likelihood that an individual will contract a pathogen as a function of contact with an infected person and/or pathogen. Additionally or alternatively, computing device may ascertain geographical predictive element 120 as a function of determining a contagion factor. As used in this disclosure a "contagion factor" is a quantitative value denoting the contagiousness of a pathogen. In an embodiment and without limitation, contagion factor may include a basic reproduction number, $R_0$. As used in this disclosure a "basic reproduction number" is the expected number of cases directly generated by one case in a population where all individuals are susceptible to infection. For example, and without limitation, Ebola may have a $R_0$ of 1.5-1.9. As a further non-limiting example, HIV/AIDS may have an $R_0$ of 2-5. For example, and without limitation a contagion factor may be less than 1, wherein a value less than 1 denotes that each infected individual may infect less than one new individual. As a further non-limiting example, a contagion factor may equal to 1, wherein a value of 1 denotes that each infected individual may infect one new individual. As a further non-limiting example, a contagion factor may greater than 1, wherein a value greater than 1 denotes that each infected individual may infect more than one new individual.

In an embodiment, and still referring to FIG. 1, computing device 104 may ascertain geographical predictive element 120 as a function of identifying a progression phase, wherein a progression phase is a phase and/or stage of a geographically linked dysfunction as described below in detail in reference to FIG. 4. For example, and without limitation, progression phase may include a/an incubation phase, prodromal phase, illness phase, decline phase, and/or convalescence phase. Progression phase may be identified as a function of identifying a pathogenic particle enumeration. As used in this disclosure a "pathogenic particle enumeration" is a quantitative value associated with a number of distinct organisms, bacteria, viruses, contagions, pathogens, and the like thereof. For example, and without limitation, pathogenic particle enumeration may include a value of 100 pathogenic particles associated with dengue fever. As a further non-limiting example, pathogenic particle enumeration may include a value of 2,000 pathogenic particles associated with malaria. Progression phase may be identified as a function of determining a severity index. As used in this disclosure a "severity index" is a measurable value associated with the signs and/or symptoms of a particular pathogen. For example, and without limitation, severity index may be a value of 27 for the symptom of a fever for a pathogen. As a further non-limiting example, severity index may be a value of 91 for the symptom of temporary paralysis and incapacitation.

In an embodiment, and still referring to FIG. 1, progression phase may be determined as a function of one or more progression machine-learning models. As used in this disclosure, a "progression machine-learning model" is a machine-learning model to produce a progression phase output given pathogenic particle enumeration and/or severity index as inputs; this is in contrast to a non-machine learning software program where the commands to be executed are determined in advance by a user and written in a programming language. Progression machine-learning model may include one or more progression machine-learning processes such as supervised, unsupervised, or reinforcement machine-learning processes that computing device 104 and/or a remote device may or may not use in the determination of progression phase. As used in this disclosure "remote device" is an external device to computing device 104. A progression machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train progression machine-learning process as a function of a progression training set. As used in this disclosure, a "progression training set" is a training set that correlates at least a pathogenic particle enumeration and a severity index to a progression phase. As a non-limiting example a pathogenic particle enumeration of 200 may be relate to a severity index of 32 wherein a progression phase of incubation phase may be outputted. The progression training set may be received as a function of user-entered valuations of pathogenic particle enumerations, severity indexes, and/or progression phases. Computing device 104 may receive progression training set by receiving correlations of pathogenic particle enumerations and/or severity indexes that were previously received and/or determined during a previous iteration of determining progression phases. The progression training set may be received by one or more remote devices that at least correlate a pathogenic particle enumeration and/or severity index to a progression phase, wherein a remote device is an external device to computing device 104, as described above. The progression training set may be received in the form of one or more user-entered correlations of a pathogenic particle enumeration and/or severity index to a progression phase. Additionally or alternatively, a user may include an informed advisor, wherein an informed advisor may include, without limitation, family physicians, tropical medicine physicians, infectious disease physicians, medical parasitologists, traveler's health physicians, and the like thereof.

Still referring to FIG. 1, computing device 104 may receive progression machine-learning model from the remote device that utilizes one or more progression machine learning processes, wherein a remote device is described above in detail. For example, and without limitation, a remote device may include a computing device, external device, processor, and the like thereof. The remote device may perform the progression machine-learning process using the progression training set to generate progression phase and transmit the output to computing device 104. The remote device may transmit a signal, bit, datum, or parameter to computing device 104 that at least relates to progression phases. Additionally or alternatively, the remote device may provide an updated machine-learning model. For example, and without limitation, an updated machine-learning model may be comprised of a firmware update, a software update, a progression machine-learning process correction, and the like thereof. As a non-limiting example a software update may incorporate a new pathogenic particle enumeration that relates to a modified severity index. Additionally or alternatively, the updated machine learning model may be transmitted to the remote device, wherein the remote device may replace the progression machine-learning model with the updated machine-learning model and determine the progression phase as a function of the pathogenic particle enumeration using the updated machine-learning model. The updated machine-learning model may be transmitted by the remote device and received by computing device 104 as a software update, firmware update, or corrected progression machine-learning model. For example, and without limitation progression machine-learning model may utilize a Naïve bayes machine-learning process, wherein the updated machine-learning model may incorporate decision tree machine-learning process.

Still referring to FIG. 1, computing device may identify progression phase as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 identifies vigor panel 112 as a function of geographical predictive element 120 and biochemical element 108 using a geographical machine-learning model 124. As used in this disclosure "geographical machine-learning model" is a machine-learning model to produce a vigor panel output given geographical predictive elements and/or biochemical elements as inputs; this is in contrast to a non-machine learning software program where the commands to be executed are determined in advance by a user and written in a programming language. Geographical machine-learning model 124 may include one or more geographical machine-learning processes such as supervised, unsupervised, or reinforcement machine-learning processes that computing device 104 and/or a remote device may or may not use in the determination of vigor panel 116, wherein a remote device is described above in detail. An geographical machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train geographical machine-learning process as a function of a geographical training set. As used in this disclosure a "geographical training set" is a training set that correlates a geographical predictive element and/or biochemical element to a vigor panel. For example, and without limitation, a geographical predictive element of a high likelihood for contracting a pathogen and a biochemical element of a fever and chills may relate to a vigor panel of an indication of a geographically linked dysfunction. The geographical training set may be received as a function of user-entered valuations of geographical predictive elements, biochemical elements, and/or vigor panels. Computing device 104 may receive geographical training set by receiving correlations of geographical predictive elements, and/or biochemical elements that were previously received and/or determined during a previous iteration of determining vigor panels. The geographical training set may be received by one or more remote devices that at least correlate a geographical predictive element and/or biochemical element to a vigor panel, wherein a remote device is an external device to computing device 104, as described above. The geographical training set may be received in the form of one or more user-entered correlations of a geographical predictive element and/or biochemical element to a vigor panel. Additionally or alternatively, a user may include an informed advisor, wherein an informed advisor may include, without limitation, family physicians, tropical medicine physicians, infectious disease physicians, medical parasitologists, traveler's health physicians, and the like thereof.

Still referring to FIG. 1, computing device 104 may receive geographical machine-learning model 124 from a remote device that utilizes one or more geographical machine learning processes, wherein a remote device is described above in detail. For example, and without limitation, a remote device may include a computing device, external device, processor, and the like thereof. Remote device may perform the geographical machine-learning process using the geographical training set to generate vigor panel 112 and transmit the output to computing device 104. Remote device may transmit a signal, bit, datum, or parameter to computing device 104 that at least relates to vigor panel 112. Additionally or alternatively, the remote device may provide an updated machine-learning model. For example, and without limitation, an updated machine-learning model may be comprised of a firmware update, a software update, a geographical machine-learning process correction, and the like thereof. As a non-limiting example a software update may incorporate a new geographical predictive element that relates to a modified biochemical element. Additionally or alternatively, the updated machine learning model may be transmitted to the remote device, wherein the remote device may replace the geographical machine-learning model with the updated machine-learning model and determine the vigor panel as a function of the geographical predictive element using the updated machine-learning model. The updated machine-learning model may be transmitted by the remote device and received by computing device 104 as a software update, firmware update, or corrected geographical machine-learning model. For example, and without limitation geographical machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Non-provisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. Additionally or alternatively, geographical machine-learning model 124 may identify the vigor panel as a function of one or more classifiers, wherein a classifier is described above in detail.

Still referring to FIG. 1, computing device 104 may identify vigor panel 116 by identifying a geographically linked dysfunction. As used in this disclosure an "geographically linked dysfunction" is an ailment and/or collection of ailments that impact an individual's health system. As a non-limiting example, geographically linked dysfunction may include Malaria, schistosomiasis, onchocerciasis, leprosy, dengue fever, tuberculosis, hookworm, HIV, leishmaniasis, lymphatic filariasis, chagas disease, trypanosomiasis, African sleeping sickness, and the like thereof. Geographically linked dysfunction may be determined as a function of one or more dysfunction machine-learning models. As used in this disclosure, a "dysfunction machine-learning model" is a machine-learning model to produce a geographically linked dysfunction output given biochemical element 108 as inputs; this is in contrast to a non-machine learning software program where the commands to be executed are determined in advance by a user and written in a programming language. Dysfunction machine-learning model may include one or more dysfunction machine-learning processes such as supervised, unsupervised, or reinforcement machine-learning processes that computing device 104 and/or a remote device may or may not use in the determination of geographically linked dysfunction. A dysfunction machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train dysfunction machine-learning process as a function of a dysfunction training set. As used in this disclosure, a "dysfunction training set" is a training set that correlates at least a geographical enumeration and a health system effect to a geographically linked dysfunction. As used in this disclosure, a "geographical enumeration" is a measurable value associated with the biochemical element. As used in this disclosure, a "health system effect" is an impact and/or effect the biochemical element has on the health system of an individual. As a non-limiting example a geographical enumeration of 79 may be relate to a health system effect of paralysis wherein a geographically linked dysfunction of leprosy may be outputted. The dysfunction training set may be received as a function of user-entered valuations of geographical enumerations, health system effects, and/or geographically linked dysfunctions. Computing device 104 may receive dysfunction training set by receiving correlations of geographical enumerations and/or health system effects that were previously received and/or determined during a previous iteration of determining geographically linked dysfunctions. The dysfunction training set may be received by one or more remote devices that at least correlate a geographical enumeration and/or health system effect to a geographically linked dysfunction, wherein a remote device is an external device to computing device 104, as described above. The dysfunction training set may be received in the form of one or more user-entered correlations of a geographical enumeration and health system effect to a geographically linked dysfunction. Additionally or alternatively, a user may include an informed advisor, wherein an informed advisor may include, without limitation, family physicians, tropical medicine physicians, infectious disease physicians, medical parasitologists, traveler's health physicians, and the like thereof.

Still referring to FIG. 1, computing device 104 may receive dysfunction machine-learning model from the remote device that utilizes one or more dysfunction machine learning processes, wherein a remote device is described above in detail. For example, and without limitation, a remote device may include a computing device, external device, processor, and the like thereof. The remote device may perform the dysfunction machine-learning process using the dysfunction training set to generate geographically linked dysfunction and transmit the output to computing device 104. The remote device may transmit a signal, bit, datum, or parameter to computing device 104 that at least relates to geographically linked dysfunctions. Additionally or alternatively, the remote device may provide an updated machine-learning model. For example, and without limitation, an updated machine-learning model may be comprised of a firmware update, a software update, a dysfunction machine-learning process correction, and the like thereof. As a non-limiting example a software update may incorporate a new geographical enumeration that relates to a modified health system effect. Additionally or alternatively, the updated machine learning model may be transmitted to the remote device, wherein the remote device may replace the dysfunction machine-learning model with the updated machine-learning model and determine the geographically linked dysfunction as a function of the geographical enumeration using the updated machine-learning model. The updated machine-learning model may be transmitted by the remote device and received by computing device 104 as a software update, firmware update, or corrected dysfunction machine-learning model. For example, and without limitation dysfunction machine-learning model may utilize a Naïve bayes machine-learning process, wherein the updated machine-learning model may incorporate decision tree machine-learning process. Additionally or alternatively, dysfunction machine-learning model may determine the geographically linked dysfunction as a function of one or more classifiers, wherein a classifier is described above in detail.

Still referring to FIG. 1, computing device 104 determines an edible 124 as a function of vigor panel 112. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may determine edible 124 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an "edible directory" is a database of edibles that may be identified as a function of one or more metabolic components, as described in detail below, in reference to FIG. 3.

Still referring to FIG. 1, computing device 104 may produce a nourishment demand as a function vigor panel 112. As used in this disclosure a "nourishment demand" is a requirement and/or necessary amount of nutrients required for a user to consume. As a non-limiting example, nourishment demand may include a user requirement of 32 g of omega-3-fatty acid to be consumed per day. Nourishment demand may be determined as a function of receiving a nourishment goal. As used in this disclosure a "nourishment goal" is a recommended amount of nutrients that a user should consume. Nourishment goal may be identified by one or more organizations that relate to, represent, and/or study addictions in humans, such as the American Medical Association, International Society for Neglected Tropical Diseases, Tropical Pathology & Infectious Disease Association, American Society of Tropical Medicine and Hygiene, Pan American Health Organization, National Organization for Rare Disorders, and the like thereof.

Still referring to FIG. 1, computing device 104 identifies edible 124 as a function of nourishment composition, nourishment demand, and an edible machine-learning model. As used in this disclosure a "edible machine-learning model" is a machine-learning model to produce an edible output given nourishment compositions and nourishment demands as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 124, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment demand to an edible. For example, and without limitation, nourishment composition of 83 mg quinine and a nourishment demand of 40 mg of quinine as a function of a malaria may relate to an edible of tonic water. The edible training set may be received as a function of user-entered valuations of nourishment compositions, nourishment demands, and/or edibles. Computing device 104 may receive edible training set by receiving correlations of nourishment compositions and/or nourishment demands that were previously received and/or determined during a previous iteration of determining edibles. The edible training set may be received by one or more remote devices that at least correlate a nourishment composition and nourishment demand to an edible, wherein a remote device is an external device to computing device 104, as described above. Edible training set may be received in the form of one or more user-entered correlations of a nourishment composition and/or nourishment demand to an edible. Additionally or alternatively, a user may include an informed advisor, wherein an informed advisor may include, without limitation, family physicians, tropical medicine physicians, infectious disease physicians, medical parasitologists, traveler's health physicians, and the like thereof.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 124 and transmit the output to computing device 104. Remote device may transmit a signal, bit, datum, or parameter to computing device 104 that at least relates to edible 124. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the edible machine-learning model with the updated machine-learning model and determine the edible as a function of the nourishment demand using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, edible machine-learning model may identify edible 124 as a function of one or more classifiers, wherein a classifier is described above in detail.

Still referring to FIG. 1, computing device 104 may identify edible as a function of a likelihood parameter. As used in this disclosure a "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of anchovies. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for beef flavor and/or chewy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database or other data structure including flavors for an edible. As a non-limiting example flavor directory may include a list and/or collection of edibles that all contain sweet flavor variables. As a further non-limiting example flavor directory may include a list and/or collection of edibles that all contain umami flavor variables. Flavor directory may be implemented similarly to an edible directory as described below in detail, in reference to FIG. 3. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 may determine edible 124 as a function of receiving an allergic response input from a user. As used in this disclosure an "allergic response input" is an input associated with a user's allergic reaction to a particular edible. For example, and without limitation, allergic response input may include an input associated with a user's allergic reaction to cow's milk, eggs, tree nuts, peanuts, shellfish, wheat, soy, fish, and the like thereof. Computing device 104 may determine a predictive allergic element as a function of allergic response input. As used in this disclosure a "predictive allergic element" is an element associated with the likelihood for a user to experience an allergic reaction. For example, and without limitation, predictive allergic element may include determining a low likelihood that an edible with 20 mg of peanuts may result in an allergic reaction for peanuts. As a further non-limiting example, predictive allergic element may include determining a high likelihood that an edible with 3 g of shellfish may result in an allergic reaction for an individual for shellfish.

Still referring to FIG. 1, computing device 104 generates a nourishment program 132 as a function of edible 124. Still referring to FIG. 1, computing device 104 generates a nourishment program 132 as a function of edible 124. As used in this disclosure a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 132 may consist of recommending papaya leaf for 4 days. As a further non-limiting example nourishment program 132 may recommend fish for a first day, broccoli for a second day, and legumes for a third day. Nourishment program 132 may include one or more diet programs such as paleo, keto, vegan, vegetarian, and the like thereof. Computing device 104 may develop nourishment program 132 as a function of an intended outcome. As used in this disclosure an "intended outcome" is an outcome that an edible may generate according to a predicted and/or purposeful plan. As a non-limiting example, intended outcome may include a treatment outcome. As used in this disclosure a "treatment outcome" is an intended outcome that is designed to at least reverse and/or eliminate vigor panel 112, biochemical element 108 and/or geographically linked dysfunction. As a non-limiting example, a treatment outcome may include reversing the effects of the geographical dysfunction schistosomiasis. As a further non-limiting example, a treatment outcome includes reversing the geographically linked dysfunction of leishmaniasis. Intended outcome may include a prevention outcome. As used in this disclosure a "prevention outcome" is an intended outcome that is designed to at least prevent and/or avert vigor panel 112, biochemical element 108 and/or geographically linked dysfunction. As a non-limiting example, a prevention outcome may include preventing the development of the geographically linked dysfunction leprosy. As a further non-limiting example a prevention outcome may include preventing the development of schistosomiasis as a function of a carnivorous diet. Intended outcome may include a mitigating outcome. As used in this disclosure a "mitigating outcome" is an intended outcome that is designed to slow and/or mitigate the development of vigor panel 112, biochemical element 108 and/or geographically linked dysfunction. As a non-limiting example, a mitigating outcome may include slowing down the development of the geographically linked dysfunction AIDS.

Still referring to FIG. 1, computing device 104 may develop nourishment program 132 as a function of edible 124 and intended outcome using a nourishment machine-learning model. As used in this disclosure a "nourishment machine-learning model" is a machine-learning model to produce a nourishment program output given edibles and/or intended outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 132. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates an intended outcome to an edible. The nourishment training set may be received as a function of user-entered edibles, intended outcomes, and/or nourishment programs. For example, and without limitation, an intended outcome of treating Chagas disease may correlate to an edible of ginger, aloe vera, and/or garlic. Computing device 104 may receive nourishment training by receiving correlations of intended outcomes and/or edibles that were previously received and/or determined during a previous iteration of developing nourishment programs. The nourishment training set may be received by one or more remote devices that at least correlate an intended outcome and/or edible to a nourishment program, wherein a remote device is an external device to computing device 104, as described above. Nourishment training set may be received in the form of one or more user-entered correlations of an intended outcome and/or edible to a nourishment program. Additionally or alternatively, a user may include an informed advisor, wherein an informed advisor may include, without limitation, family physicians, tropical medicine physicians, infectious disease physicians, medical parasitologists, traveler's health physicians, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 132 and transmit the output to computing device 104. The remote device may transmit a signal, bit, datum, or parameter to computing device 104 that at least relates to nourishment program 132. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new intended outcome that relates to a modified edible. Additionally or alternatively, the updated machine learning model may be transmitted to the remote device, wherein the remote device may replace the nourishment machine-learning model with the updated machine-learning model and develop the nourishment program as a function of the intended outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

With continued reference to FIG. 1, computing device 104 may be configured to receive a biological response of a user as a function of implementing nourishment program 132. As used in this disclosure a "biological response" is a response from the user regarding the efficacy of nourishment program 132. Biological response may include any information about nourishment program 132. For example, and without limitation, biological response may include a user's consistency with nourishment program 132. As a further non-limiting example, biological response may include one or more vigor panel improvements and/or biochemical element alterations. As a further non-limiting example, biological response may include one or more user preferences, likes and/or dislikes of nourishment program 132. Biological response may also describe a user's current feelings and/or opinions of nourishment program 132. Biological response may describe a user's geographically linked dysfunction is better controlled and/or maintained as a function of one or more third-party evaluations. Computing device 104 may update a nourishment program 124 based on a biological response. Updating nourishment program 132 may include any method as described above in detail for generating nourishment program 132.

Figure 2:
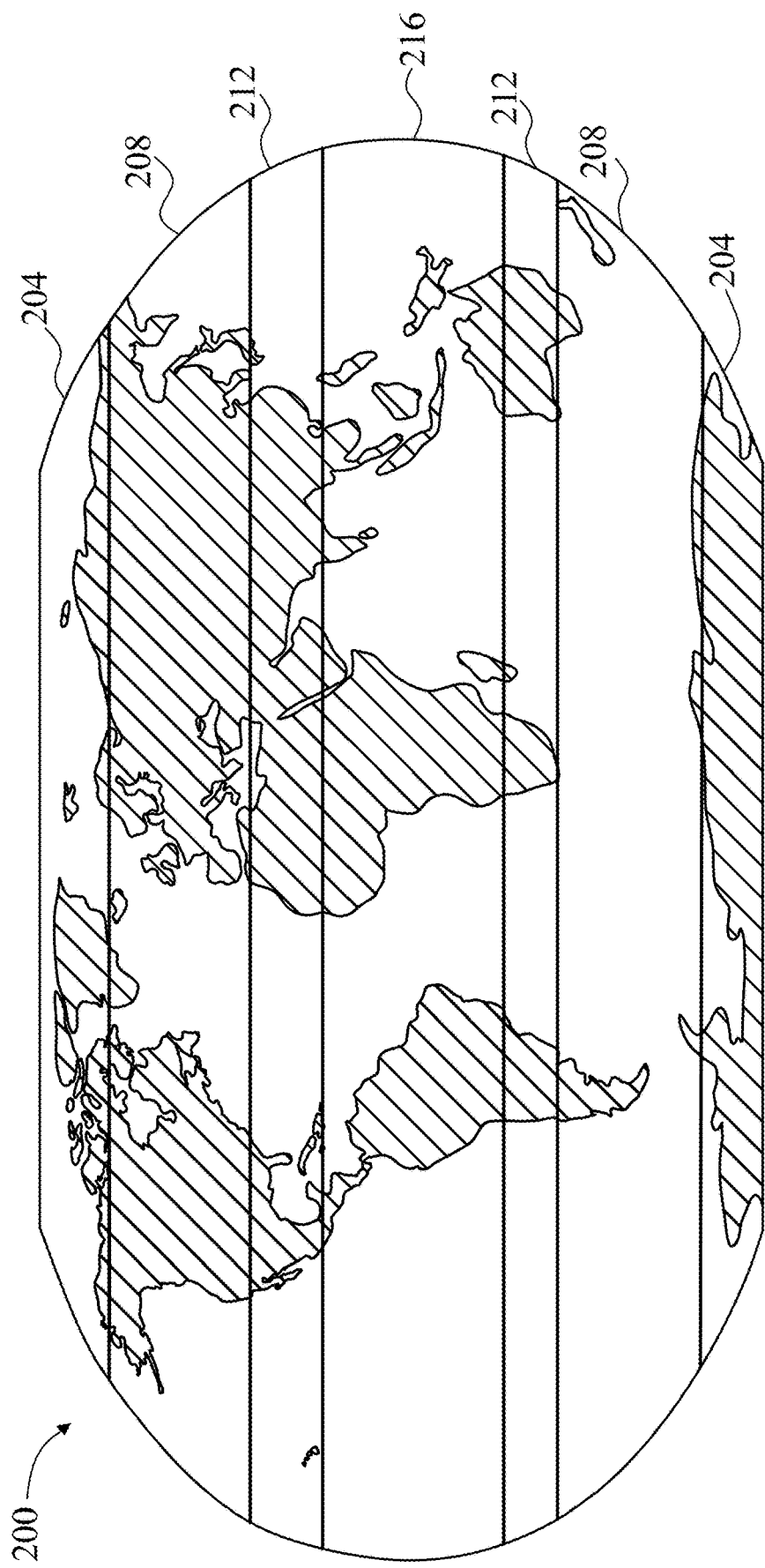
FIG. 2 is a block diagram of an exemplary embodiment of a geographical location according to an embodiment of the invention.

Now referring to FIG. 2 an exemplary embodiment 200 of a geographical location is illustrated. As used in this disclosure a "geographical location" is a location and/or place used to denote a region on the earth's surface or elsewhere. As a non-limiting example, geographical location may include one or more longitudes and/or latitudes of a user. Geographical location may include an arctic zone 204. As used in this disclosure an "arctic zone" is a zone between 60° latitude and 90° latitude. Arctic zone 204 may include one or more regions where pathogens associated with *Streptococcus pneumoniae, Hemophilus influenzae*, tuberculosis, chronic otitis media, hepatitis B virus, sexually transmitted infections, *Helicobacter pylori*, parasitic infections, bacterial zoonoses, and the like thereof may be prevalent. Geographical location may include a temperate zone 208. As used in this disclosure a "temperate zone" is a zone between 40° latitude and 60° latitude. Temperate zone 208 may include one or more regions where pathogens associated with hepatitis B, influenza A, measles, pertussis, rotavirus A, syphilis, tetanus and tuberculosis, and the like thereof may be prevalent. Geographical location may include a subtropical zone 212. As used in this disclosure a "subtropical zone" is a zone between 23° latitude and 40° latitude. Subtropical zone 212 may include one or more regions where pathogens associated with dengue fever, malaria, leishmaniasis, *Entamoeba histolytica*, hookworms, and the like thereof may be prevalent. Geographical location may include a tropical zone 216. As used in this disclosure a "tropical zone" is a zone between 23° latitude in the northern hemisphere and 23° latitude in the southern hemisphere. Tropical zone 216 may include one or more regions where pathogens associated with arbovirus, dengue fever, yellow fever, rotavirus, AIDS, Ebola, Marburg virus, Lassa fever, cholera, *Escherichia coli*, tuberculosis, Hansen's disease, malaria, leishmaniasis, trypanosomiasis, *Trypanosoma cruzi*, schistosomiasis, filariasis, *Toxoplasma gondii*, *Trichomonas vaginalis*, hookworms, *ascaris*, buruli ulcers, Chagas disease, cysticercosis, dracunculiasis, echinococcosis, fascioliasis, leprosy, lymphatic filariasis, mycetoma, onchocerciasis, rabies, trachoma, and the like thereof may be prevalent.

Figure 3:
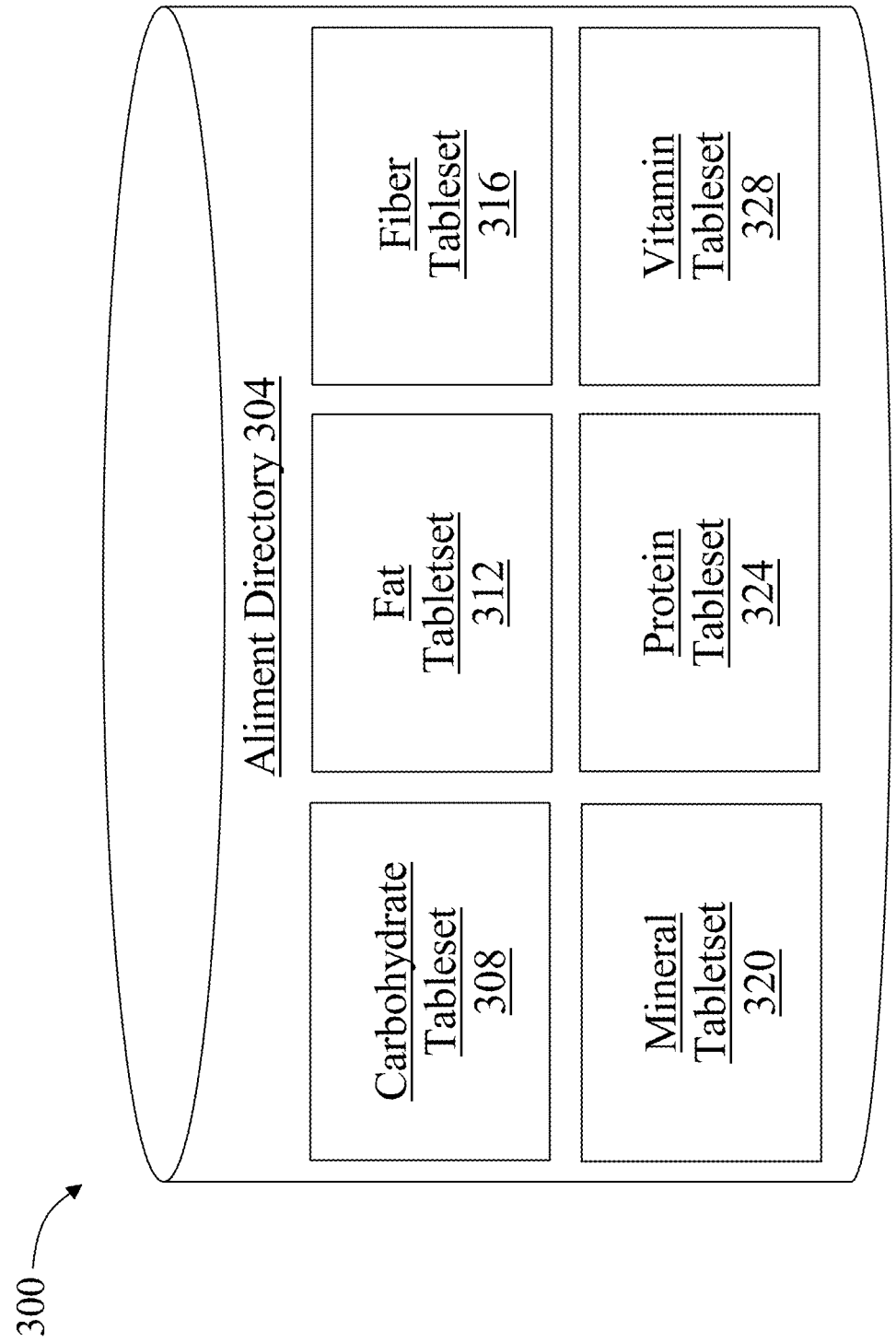
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, *psyllium*, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
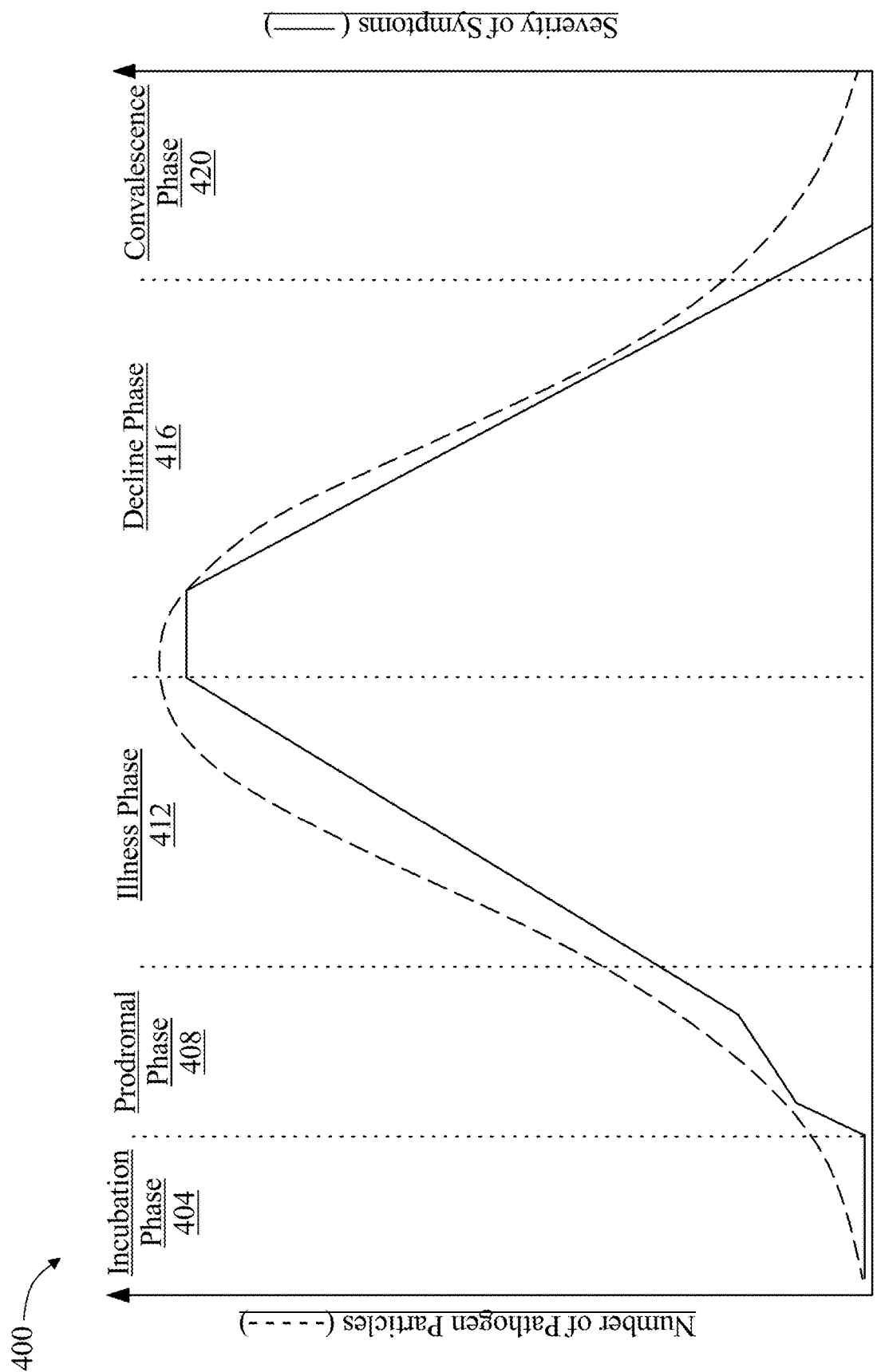
FIG. 4 is a block diagram of an exemplary embodiment of a progression phase according to an embodiment of the invention.

Now referring to FIG. 4, an exemplary embodiment 400 of a progression phase is illustrated. As used in this disclosure a "progression phase" is a phase and/or stage of a geographically linked dysfunction. Progression phase may include an incubation phase 404. As used in this disclosure an "incubation phase" is a phase after the initial entry of a pathogen, wherein a pathogen is a bacterium, virus, or other microorganism that can cause disease, as described above in detail in reference to FIG. 1. In an embodiment, and without limitation incubation phase 404 may include a phase where the pathogen begins multiplying in the user but does not present signs and/or symptoms of a dysfunction. Progression phase may include a prodromal phase 308. As used in this disclosure a "prodromal phase" is a phase after the incubation phase. As a non-limiting example, prodromal phase 408 may include a phase when the pathogen continues to multiply, and the host begins to experience general signs and symptoms of the dysfunction due to activation of the immune system. Prodromal phase 408 may include, without limitation, signs and symptoms that are general such as fever, pain, soreness, swelling, inflammation, and the like thereof. Progression phase may include an illness phase 412. As used in this disclosure an "illness phase" is a phase after the prodromal phase where the signs and symptoms of the dysfunction are obvious and severe for an individual. As a non-limiting example, illness phase 412 may include one or more phases where the severity of the symptoms rapidly increases to the maximum severity. Progression phase may include a decline phase 416. As used in this disclosure a "decline phase" is a phase after the illness phase where the number of pathogen particles beings to decrease. Decline phase 416 may include, without limitation, a phase when the signs and symptoms of the dysfunction begin to decline. In an embodiment, and without limitation, decline phase 416 may include one or more susceptibility elements, wherein a "susceptibility element", as used herein, is an element associated with a higher propensity for developing a secondary dysfunction. For example, and without limitation, susceptibility element may include one or more elements of a user's weakened immune system because of the primary dysfunction, wherein the user may be susceptible to a secondary dysfunction. Progression phase may include a convalescence phase 420. As used in this disclosure a "convalescence phase" is a final phase of a dysfunction. Convalescence phase 420 may include a phase in which the user returns to normal bodily functions.

Figure 5:
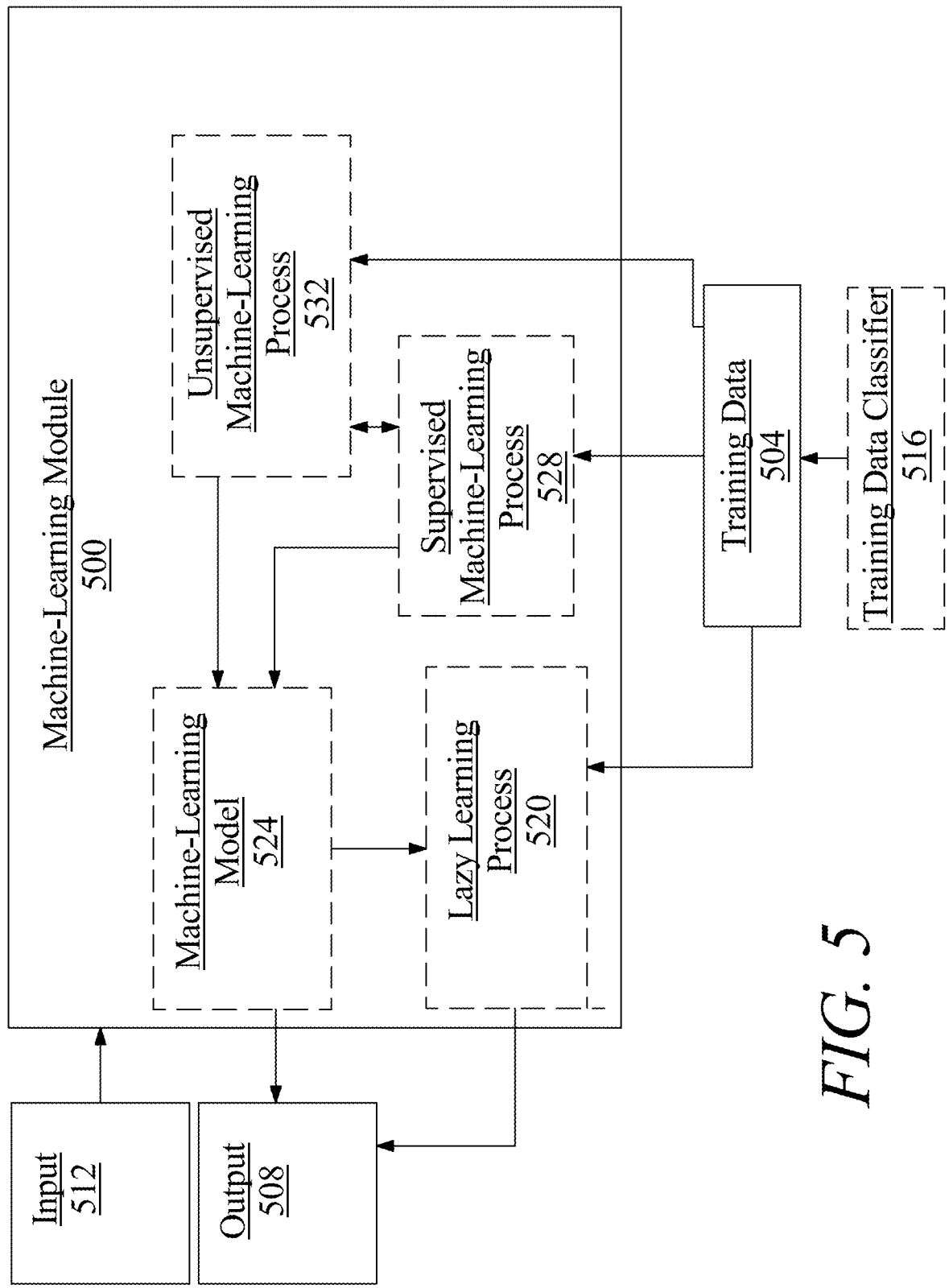
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs such as geographical predictive elements and/or biochemical elements may result in outputs such as a vigor panel.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of biochemical elements such as biomarkers, inputs, assessments, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include geographical predictive elements and/or biochemical elements as described above as inputs, vigor panels as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
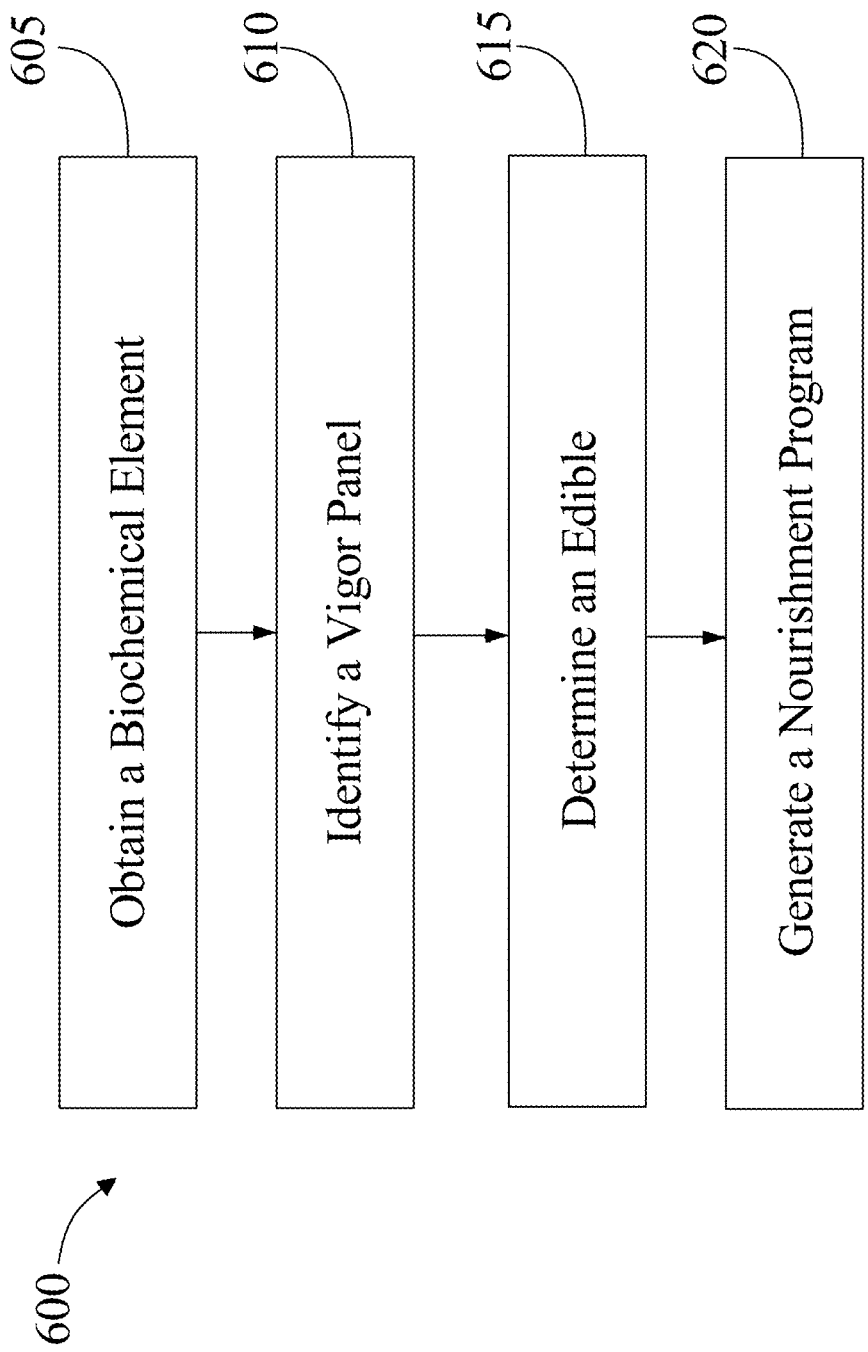
FIG. 6 is a process flow diagram illustrating an exemplary embodiment of a method of generating a geographically linked nourishment program.

Now referring to FIG. 6, an exemplary embodiment of a method 600 for generating a geographically linked nourishment program is illustrated. At step 605, a computing device 104 obtains a biochemical element 108. Computing device 104 includes any of the computing device 104 as described above, in reference to FIGS. 1-5. Biochemical element 108 includes any of the biochemical element 108 as described above, in reference to FIGS. 1-5.

Still referring to FIG. 6, at step 610, computing device 104 identifies a vigor panel 112 as a function of biochemical element 108. Vigor panel 112 includes any of the vigor panel 112 as described above, in reference to FIGS. 1-5. Computing device 104 identifies vigor panel 112 by receiving a geographical indicator 116. Geographical indicator 116 includes any of the geographical indicator 116 as described above, in reference to FIGS. 1-5. Computing device 104 identifies vigor panel 112 by ascertaining a geographical predictive element 120 as a function of geographical indicator 116. Geographical predictive element 120 includes any of the geographical predictive element 120 as described above, in reference to FIGS. 1-5. Computing device 104 identifies vigor panel 112 as a function geographical predictive element 120 and biochemical element 108 using a geographical machine-learning model 124. Geographical machine-learning model 124 includes any of the geographical machine-learning model 124 as described above, in reference to FIGS. 1-5.

Still referring to FIG. 6, at step 615, computing device 104 determines an edible 124 as a function of vigor panel 112. Edible 124 includes any of the edible 124 as described above, in reference to FIGS. 1-5.

Still referring to FIG. 6, at step 620, computing device 104, generates a nourishment program 132 as a function of edible 124. Nourishment program 132 includes any of the nourishment program 132 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
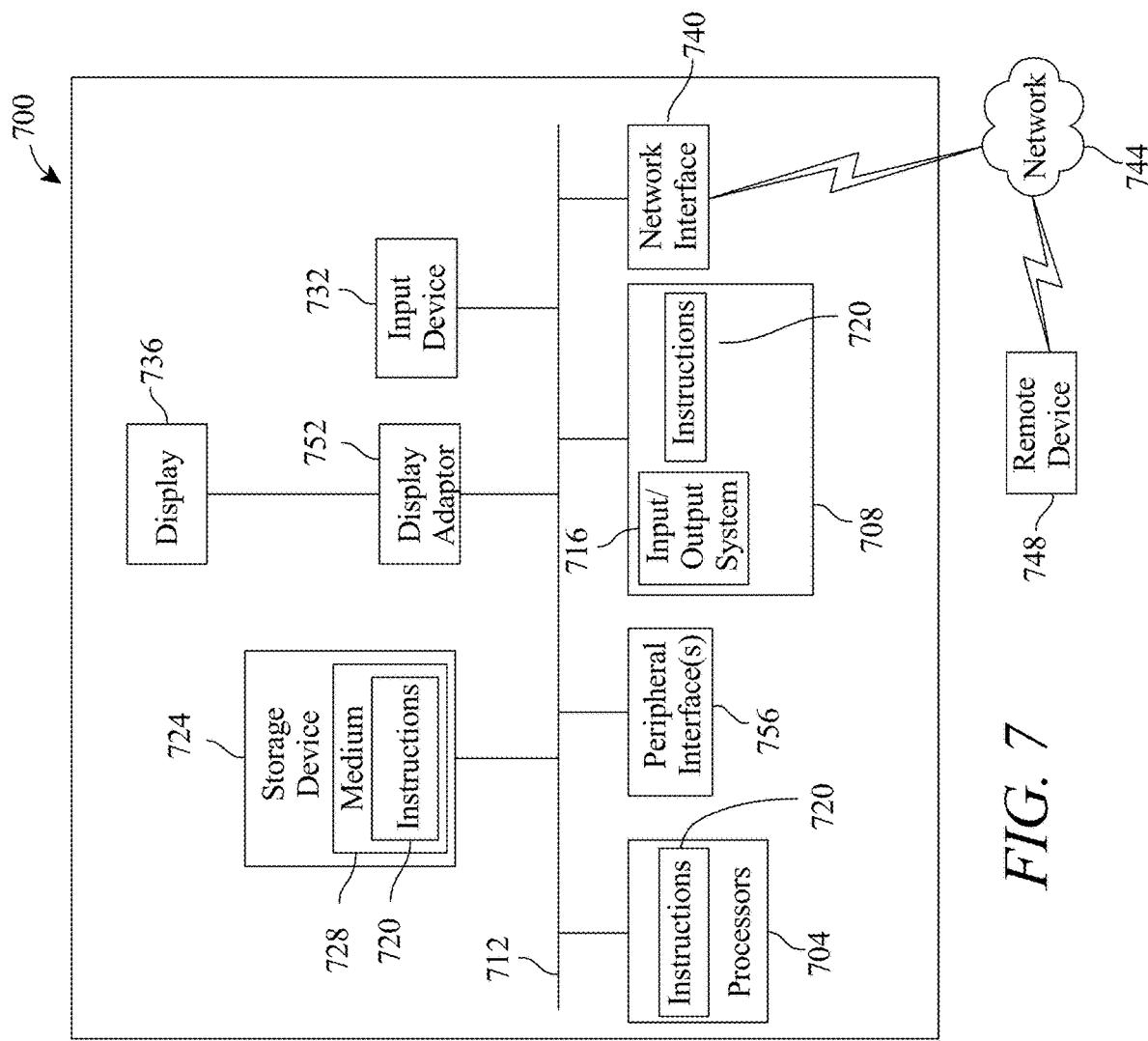
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a geographically linked nourishment program, the system comprising:
   a computing device, the computing device configured to:
      obtain a biochemical element of a user;
      receive a geographical indicator of the user;
      identify a pathogenic particle enumeration of the user;
      train a progression machine-learning model, wherein the progression machine-learning model is trained using progression training set, wherein training the progression machine-learning model further comprises:
         applying the progression training set to an input layer of nodes comprising at least the pathogenic particle enumeration, one or more intermediate layers of nodes, and an output layer of nodes comprising a progression phase output;
         adjusting one or more connections and one or more weights between nodes in adjacent layers of the progression machine-learning model;
         detecting additional correlations between the output layer of nodes and the input layer of nodes;
         iteratively training the progression machine-learning model as a function of the detected additional correlations;
      determine a progression phase as a function of the trained progression machine-learning model, wherein determining the progression phase comprises: determining a severity index of the user; and
      identifying the progression phase as a function of the pathogenic particle enumeration and the severity index using a progression classifier identify a vigor panel as a function of the biochemical element, the progression phase determined using the trained progression machine-learning model and the progression classifier and a geographical predictive element determined as a function of the progression phase, wherein identifying the vigor panel comprise:
identifying the vigor panel as a function of the geographical predictive element determined as a function of the progression phase determined using the trained progression machine-learning model and the progression classifier and the biochemical element using a geographical machine-learning model which further comprises: receiving a geographical training data set, wherein the
geographical training data set comprises a plurality of geographical predictive elements and biochemical elements correlated to the vigor panel;
training, iteratively, the geographical machine-learning model using the geographical training data set, wherein training the geographical machine-learning model includes retraining the geographical machine-learning model with feedback from previous iterations of the geographical machine-learning model; and
identifying the vigor panel as a function of the trained geographical machine-learning model and the geographical predictive element and the biochemical element;
determine an edible for the user as a function of the vigor panel;
receive an intended outcome as a function of the determined edible; and generate a nourishment program as a function of the edible and the intended
outcome using a nourishment machine-learning model which comprises: receiving a nourishment training data set, wherein the nourishment
training data set comprises a plurality of edibles and intended outcomes correlated to a plurality of nourishment programs;
training, iteratively, the nourishment machine-learning model using the nourishment training data set, wherein training the nourishment machine-learning model includes retraining the nourishment machine-learning model with feedback from previous iterations of the nourishment machine-learning model; and
identifying the nourishment program as a function of the trained nourishment machine-learning model.

2. The system of claim 1, wherein the geographical indicator includes a contact tracing element.

3. The system of claim 1, wherein ascertaining the geographical predictive element further comprises determining a contagion factor and ascertaining the geographical predictive element as a function of the contagion factor.

4. The system of claim 1, wherein identifying the vigor panel further comprises determining an origination element and identifying the vigor panel as a function of the origination element.

5. The system of claim 1, wherein identifying the vigor panel includes determining a geographically linked dysfunction and identifying the vigor panel as a function of the geographically linked dysfunction.

6. The system of claim 5, wherein determining the geographically linked dysfunction further comprises:
obtaining a dysfunction training set that correlates at least a geographical enumeration and a health system effect to the geographically linked dysfunction; and
determining the geographically linked dysfunction as a function of the biochemical element and using a dysfunction machine-learning model, wherein the dysfunction machine-learning model is trained as a function of the dysfunction training set.

7. The system of claim 1, wherein determining the edible further comprises:
receiving a nourishment composition from an edible directory;
producing a nourishment demand as a function of the vigor panel; and
determining the edible as a function of the nourishment composition and the nourishment demand using an edible machine-learning model.

8. A method for generating a geographically linked nourishment program, the method comprising:
obtaining, by a computing device, a biochemical element of a user; receiving, by the computing device, a geographical indicator of the user;
identifying, by the computing device, a pathogenic particle enumeration of the user; training, by the computing device, a progression machine-learning model, wherein the
progression machine-learning model is trained using progression training set, wherein training the progression machine-learning model further comprises:
applying the progression training set to an input layer of nodes comprising at least
the pathogenic particle enumeration, one or more intermediate layers of nodes, and an output layer of nodes comprising a progression phase output;
adjusting one or more connections and one or more weights between nodes in adjacent layers of the progression machine-learning model;
detecting additional correlations between the output layer of nodes and the input layer of nodes;
iteratively training the progression machine-learning model as a function of the detected additional correlations;
determining, by the computing device, a progression phase as a function of the trained progression machine-learning model, wherein determining the progression phase comprises:
determining a severity index of the user; and
identifying the progression phase as a function of the pathogenic particle enumeration and the severity index using a progression classifier;
identifying, by the computing device, a vigor panel as a function of the biochemical element, the progression phase determined using the trained progression machine-learning model and the progression classifier and a geographical predictive element determined as a function of the progression phase, wherein identifying the vigor panel comprises:
identifying the vigor panel as a function of the geographical predictive element determined as a function of the progression phase determined using the trained progression machine-learning model and the progression classifier and the biochemical element using a geographical machine-learning model which further comprises:
receiving a geographical training data set, wherein the geographical training data set comprises a plurality of geographical predictive elements and biochemical elements correlated to the vigor panel;

training, iteratively, the geographical machine-learning model using the geographical training data set, wherein training the geographical machine-learning model includes retraining the geographical machine-learning model with feedback from previous iterations of the geographical machine-learning model; and identifying the vigor panel as a function of the trained geographical machine-learning model and the geographical predictive element and the biochemical element;

determining, by the computing device, an edible for the user as a function of the vigor panel;

receiving, by the computing device, an intended outcome as a function of the determined edible; and generating, by the computing device, a nourishment program as a function of the edible and the intended outcome using a nourishment machine-learning model which comprises:

receiving a nourishment training data set, wherein the nourishment training data set comprises a plurality of edibles and intended outcomes correlated to a plurality of nourishment programs;

training, iteratively, the nourishment machine-learning model using the nourishment training data set, wherein training the nourishment machine learning model includes retraining the nourishment machine-learning model with feedback from previous iterations of the nourishment machine-learning model; and identifying the nourishment program as a function of the trained
nourishment machine-learning model.

9. The method of claim 8, wherein the geographical indicator includes a contact tracing element.

10. The method of claim 8, wherein ascertaining the geographical predictive element further comprises determining a contagion factor and ascertaining the geographical predictive element as a function of the contagion factor.

11. The method of claim 8, wherein identifying the vigor panel further comprises determining an origination element and identifying the vigor panel as a function of the origination element.

12. The method of claim 8, wherein identifying the vigor panel includes determining a geographically linked dysfunction and identifying the vigor panel as a function of the geographically linked dysfunction.

13. The method of claim 12, wherein determining the geographically linked dysfunction further comprises:

obtaining a dysfunction training set correlates at least a geographical enumeration and a health system effect to the geographically linked dysfunction; and determining the geographically linked dysfunction as a function of the biochemical element and using a dysfunction machine-learning model, wherein the dysfunction machine-learning model is trained as a function of the dysfunction training set.

14. The method of claim 11, wherein determining the edible further comprises:

receiving a nourishment composition from an edible directory;

producing a nourishment demand as a function of the vigor panel; and determining the edible as a function of the nourishment composition and the nourishment demand using an edible machine-learning model.

* * * * *